United States Patent [19]

Rogier

[11] 4,319,049
[45] Mar. 9, 1982

[54] BIS HYDROXYMETHYL TRICYCLO (5,2,1,0<sup>2,6</sup>) DECANE

[75] Inventor: Edgar R. Rogier, Minnetonka, Minn.

[73] Assignee: Henkel Corporation, Minneapolis, Minn.

[21] Appl. No.: 194,172

[22] Filed: Oct. 6, 1980

[51] Int. Cl.$^3$ .................... C07C 47/40; C07C 31/00; C07C 31/27

[52] U.S. Cl. .................................. 568/445; 568/817; 528/75

[58] Field of Search ............................ 568/817, 445

[56] References Cited

U.S. PATENT DOCUMENTS

| | | | |
|---|---|---|---|
| 2,841,614 | 7/1958 | Buchner et al. | 568/817 |
| 2,850,536 | 9/1958 | Buchner et al. | 568/817 |
| 3,590,086 | 6/1971 | Gourse | 568/445 |
| 4,123,394 | 10/1978 | Skorianetz et al. | 568/817 |
| 4,225,515 | 9/1980 | Weber et al. | 568/445 |

*Primary Examiner*—Joseph E. Evans
*Attorney, Agent, or Firm*—Forrest L. Collins; Patrick J. Span

[57] ABSTRACT

The present invention discloses tricyclic compounds having a gem-bis(hydroxymethyl) functional group. Compounds within the formulae of the present invention include those components having unsaturation in the ring structure and those in which the unsaturation has been converted a halogen or phosphite functionality.

4 Claims, No Drawings

BIS HYDROXYMETHYL TRICYCLO (5,2,1,0$^{2,6}$) DECANE

BACKGROUND OF THE INVENTION

1. Field of the Invention

The present invention describes polycyclic compounds having a gem bis(hydroxymethyl) structure which may be utilized for curing into various thermoplastic or thermosetting compositions. The compounds may also be reactive through retaining unsaturation within the molecule, may be saturated, or may be derivatized with a halogen or phosphite to obtain fire retardant properties.

2. Description of the Art Practice

Various tricyclic compounds are described in U.S. Pat. No. 3,470,248 issued Sept. 30, 1969 to Brotherton et al. The materials described in the Brotherton et al patent are stated to be useful in the resin art such as in the preparation of urethane polymers, polyamides and polyurethane polyurea elastomers. U.S. Pat. No. 3,787,371 issued Jan. 22, 1974 to Brinkmann et al discloses similar compounds which are stated to be useful in the formation of clear polyamides.

U.S. Pat. 3,317,469 issued May 2, 1967 to Feichtinger et al also discloses the use of materials similar to those in the Brotherton patent. Wagner et al in German OLS 2641662 published Mar. 23, 1978 also discloses tricyclodecane derivatives which have been functionalized. British Pat. No. 1,266,016 published Mar. 8, 1972 discloses tricyclodecane curing agent. Japanese published patent application No. 54-4992 published Jan. 16, 1979 naming Kaya as an inventor also describes polycyclic compounds.

An unpublished disclosure concerning such compounds is found in U.S. Pat. application Ser. No. 074,368 filed Sept. 10, 1979 which is the invention of the author of this patent. Additional work concerning such compounds is found in the disclosures of Fujikura et al Synthetic Communications Volume 6 No. 3 pages 199-207 (1976). Further disclosures of such technology concerning polycyclic compounds is found in Pruett, Ann. N.Y., Acad. Sci. Volume 295 pages 239-248 (1977).

Additional polycylic compounds are disclosed in OLS No. 2,200,022 published July 19, 1973 by Gierenz et al. Still further technology involving polycyclic compounds is found OLS No. 2,307,627 published Sept. 5, 1974 by Grau. OLS. No. 2,013,316 published October 1, 1979 by von Bornhaupt also discloses polycyclic derivatives having hydroxyl functionality.

German Pat. No. 934,889 granted Nov. 19, 1955 to Roelen et al discloses polyesters of certain polycyclic compounds. German Pat. No. 1,694,868 granted February 19, 1972 to Jellienk et al discloses the use of polycyclic polyhydroxyl functional compounds in the preparation of urethanes.

Polycyclics compounds which are used to prepare unsaturated esters such as with maleic acid are disclosed in OLS No. 1,916,287 dated Oct. 15, 1970 Kolbel et al.

Several additional polycyclic compounds are disclosed in OLS No. 2,200,021 laid open July 26, 1973, noting Vegemund as an inventor discloses additional polycyclic polyfunctional compounds.

Canadian Pat. No. 893,716 to Falbe issued Feb. 22, 1972 also discloses aldehydes manufactured from polycyclic compounds. Conjugated unsaturated compounds, which are polycyclic in nature, are described in U.S. Pat. 4,143,065 issued Mar. 6, 1979 to Hoffmann et al. Additional compounds of interest to chemists studying polycyclic materials is U.S. Pat. No. 4,146,505 issued Mar. 27, 1979 to Weber et al. Certain aldehydes of polycyclic compounds are also disclosed in British Pat. No. 734,030 published July 2, 1955. Canadian Pat. No. 867,229 also describes the production of polycyclic polyols in an application published May 3, 1961.

Nyi in U.S. Pat. No. 4,140,724 describes certain polycyclic monoethers in a patent granted February 20, 1979. In U.S. Pat. No. 4,117,030 issued Sept. 26, 1978 to Nelson several additional polycyclic compounds having various functional groups are disclosed.

Even though substantial work has been done in the area of polycyclic compounds, it is not yet been recognized that superior properties may be obtained from the geminal bis(hydroxymethyl) structure on the polycyclic compounds of the present invention and, if desired, thereafter derivatizing said compounds to form fire retardant materials.

Throughout the specification in claims, percentages and ratios are given by weight and temperatures are in degrees of Celsius unless otherwise indicated. To the extent that each of the foregoing references is applicable to the present invention, it is specifically herein incorporated by reference and citation by the examiner is requested.

SUMMARY OF THE INVENTION

The present invention claims as a new composition of matter an 8,8(9,9)-bis(hydroxymethyl) tricyclo compound as shown below and hereafter described:

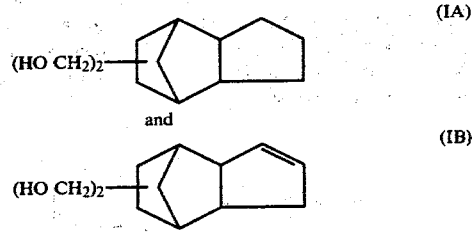

and mixtures thereof.

DETAILED DESCRIPTION OF THE INVENTION

The present invention claims a series of compounds obtained as shown above in the specification.

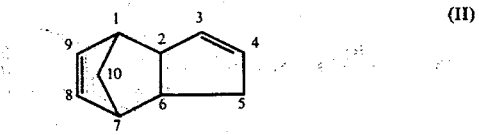

Compound II shows the basic numbering system for dicyclopentadiene and dicyclopentadiene derivatives.

The parent dicyclopentadiene compound is reacted with hydrogen and carbon monoxide under selective conditions to place a formyl group on either the 8th or 9th carbon atoms and to place a hydrogen on the remaining carbon atom. The reaction conditions as hereafter described are quite selective so that the remaining bond between the 3rd and 4th carbon atom is not affected by this reaction. This is particularly important in that it is desired that that bond should remain intact to allow for conversion to the (3 or 4) chloro or bromo and the 3(4) phosphonate derivatives. It is also noted that the unsaturation between the 3rd and 4th carbon atoms is, of course, useful as an additional material to form an oxirane at the 3-4 position.

After the formyl group has been added in the 8(9) position, formaldehyde is employed to convert the formyl group to a hydroxymethyl formyl moeity. This, of course, does not change the positioning of the formyl group on the ring structure. The conditions for reactions with formaldehyde are also selected such that the unsaturation in the 3-4 position is not disturbed. After obtaining the hydroxymethyl formyl functionality in the 8(9) position, the remaining formyl group may be reduced to give the gem bis(hydroxymethyl) structure. The gem bis(hydroxymethyl) compound is properly named 8,8(9,9) bis(hydroxymethyl) tricyclo (5,2,1,0$^{2,6}$) dec-3-ene. The reduction to give the geminal compounds may be accomplished through using an additional mole of formaldehyde under alkaline conditions or the reduction may be done utilizing materials such as sodium borohydride.

The suggested conditions for adding the gem bis(hydroxymethyl) group to the polycyclic compounds of the present invention involves hydroformylation of the 8-9 double bond to obtain the desired monoformyl compound. Conveniently, however, a slight stoichiometric excess may be added to ensure completeness of the reaction. The mixture of hydrogen and carbon monoxide for the hydroformylation reaction is conveniently maintained with respect to one another at from about 1.5:0.5 to about 0.5:1.5 on a molar ratio. It is noted that this ratio is not critical as long as the pressure is maintained in the reaction vessel by the component gases and that the amount of hydrogen is not so great as to substantially reduce any of the unsaturation in the ring system. The reaction sequence to obtain the end products is shown below.

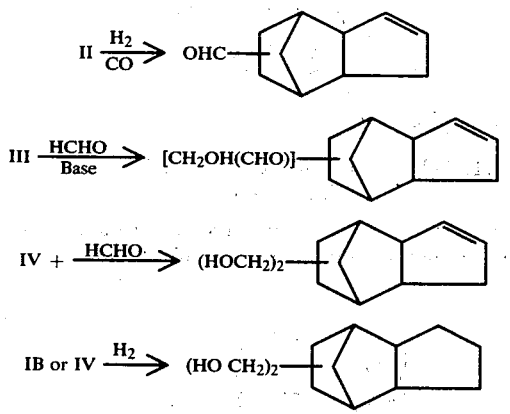

The hydroformylation is accomplished most conveniently utilizing a catalyst such as rhodium. The source of rhodium catalyst may be rhodium chloride, rhodium dicarbonyle chloride dimer, rhodium nitrate, rhodium trichloride and other materials. The ligand form from the phosphine or phosphite are conveniently trisubstituted using an alkyl or aryl compound. Conveniently, the compound is aryl and is phenyl. Several additional ligands are discussed in Selective Hydroformylation of Unsaturated Fatty Acid Esters by Frankel in the Annals N.Y. Academy of Sciences 214:79 (1973) herein incorporated by reference. Suitable examples of such catalysts include any form of rhodium preferably with a ligand such as a trialkyl amine, triphenylphosphite or triphenylphosphine.

The conditions for the pressure and temperature during the hydroformylation are conveniently conducted at from about 70 degrees C. to 100 degrees C., preferably from about 80 degrees C. to 90 degrees C. The pressure conditions within the reaction vessel are conveniently maintained at from about 10 to 150 atmospheres, preferably from 80 to 100 atmospheres absolute.

The hydroformylated reaction product is then isolated conveniently using distillation leaving the residue containing the expensive catalyst. The formyl product (III) obtained from the hydroformylation is then reacted in the presence of base with formaldehyde to give the corresponding hydroxymethyl formyl compound (IV). While it is stated that the reaction may proceed utilizing weak base, it is just as convenient to utilize two moles of formaldehyde and strong base such as sodium hydroxide to push the reaction all the way to the gem-bis(hydroxymethyl) product (IB).

The reaction to obtain the hydroxymethyl formyl compound is best conducted in an inert atmosphere, particularly nitrogen. The gem-bis(hydroxymethyl) polycyclic compound so formed is washed with water to remove any excess caustic and salts formed and then obtained in a relatively pure state by distillation.

An alternative method of accomplishing the formation of the gem-bis(hydroxymethyl) polycyclic compounds is by utilizing only one-half the equivalent amount of formaldehyde required to obtain the gem-bis(hydroxymethyl) product directly. That is, the formyl compound is converted to the corresponding hydroxymethyl formyl polycyclic compound and is then reduced using sodium borohydride or lithium aluminum hydride. The gem-bis(hydroxymethyl) compounds of the present invention may be used to prepare urethane coatings and castings. For example, a urethane coating system may be formed by reacting the hydroxyls of IA or IB with a polyfunctional isocyanate to obtain the urethane linkage.

The gem-bis(hydroxymethyl) unsaturated compounds of the present invention may be hydrogenated to give the saturated gem-bis(hydroxymethyl) structure (IA). Such saturated gem-bis(hydroxymethyl) alcohols are useful where it is not desired to have unsaturation in the backbone of the particular composition, e.q. polyurethane or polyester. Compound IV has the potentials of being present as both the endo and exo isomers are useful where both hydroxyl and aldehyde functionality are desired.

The following are suggested examples of the invention.

EXAMPLE I

PREPARATION OF 8(9)FORMYLTRICYCLO [5,2,1,0$^{2,6}$] DEC-3-ENE (III)

Into a 1 liter 316 SS autoclave was placed 105 g of dicyclopentadiene, 351 g of toluene, 1.0 g of 5% rhodium on alumina (Englehardt Industries) and 0.34 g of triphenylphosphite. The autoclave is purged with nitrogen then charged with a 1:1 mixture of carbon monoxide-hydrogen to a pressure of 65 atmospheres. The autoclave is heated, with stirring, to about 70-80 degrees C. where gas uptake begins. The temperature was maintained between 80-90 degrees C. at 70 atmospheres for 1.7 hours. The autoclave is cooled to 50 degrees and the product discharged through a filter. Distillation of the solvent produced 122 g of (III) having a carbonyl equivalent weight of 170. Infra-red and NMR spectra confirmed III as the correct structure: G.C. analysis of this product showed 96% of III and 2.3% of diformyl-tricyclodecane derivatives.

EXAMPLE II

PREPARATION OF 8,8(9,9)-BIS(HYDROXYMETHYL)-TRICYCLO [5,21,0$^{2,6}$] DEC-3-ENE (IB).

Into a 250 ml, 3-necked flask is placed 77.6 g of the aldehyde (III), 57.8 g of a 55 percent solution of formaldehyde in methanol. The solution is cooled to 11 degrees C. and 1 ml of 40 percent aqueous sodium hydroxide solution is added with stirring. The reaction mixture is gradually warmed to 45 degrees C. over a period of one hour. Stirring is continued and 40 ml of 40 percent sodium hydroxide solution is added over a period of 47 minutes during which time the temperature is maintained at 45-62 degrees C. The reaction mixture is stirred for about three hours more and the temperature allowed to fall to 36 degrees. Near the end of this time, 13 ml of a 12 percent solution of sodium borahydride in aqueous sodium hydroxide is added to convert any remaining intermediate (IV) to IB.

The reaction mixture is then stripped of methanol and water at 42 degrees C. (vacuum). The residue material is dissolved in a hot mixture of 200 ml toluene and 200 ml water. The hot toluene layer is separated and washed with water until neutral. Distillation of the toluene under reduced pressure yields 87.3 g of (IB) containing about 15 percent of 8(9)-hydroxymethyl tricyclo [5,2,1,0$^{2,6}$] dec-3-ene.

Fractional distillation of similar sample of crude IB yielded IB of 99 percent purity (GC), b.p. 165 degrees (0.5 torr), m.p. 87 degrees.

Compound IB is hydrogenated to give Compound IA by adding into a Parr reaction apparatus 19.4 grams of Compound IB in 100 ml of absolute ethanol. One gram 5 percent pallidium or carbon is then added and the system is sealed and flushed with nitrogen. Hydrogen gas is added at 4 atmospheres pressure and the flask is shaken until gas uptake is complete (about 1 hour). The catalyst is removed by filtration and Compound IA is recovered by evaporation of the ethanol. 19.3 grams of product (IA) is recovered and has a melt point of 105 degrees C.

EXAMPLE III

Compound IB is formed into a polyurethane film by reacting IB with L2291A, an aliphatic trifunctional isocyanate from Mobay in a 1:1 equivalent ratio.

The film is cured at 66 degrees C. for four hours on a Bondenite 1000 substrate at a 2 ml thickness. The pencil hardness is 2H-3H.

What is claimed is:

1. The present invention claims as a new composition of matter an 8,8(9,9)-bis(hydroxymethyl) tricyclo compound as shown below:

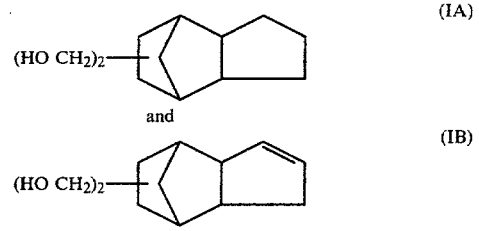

and mixtures thereof.

2. 8,8(9,9)-bis(hydroxymethyl)-tricyclo[5,2,1,0$^{2,6}$] dec-3-ene.

3. 8,8(9,9)-bis(hydroxymethyl)-tricyclo[5,2,1,0$^{2,6}$] decane.

4. 8(9)-hydroxymethyl-8(9)-formyl-tricyclo[5,2,1,0$^{2,6}$] dec-3-ene.

* * * * *